United States Patent [19]

Behring

[11] 4,256,457

[45] Mar. 17, 1981

[54] CONTAINER FOR DENTAL EQUIPMENT FOR ROOT-TREATMENT

[76] Inventor: Horst Behring, Struckholt 8B, 2000 Hamburg 63, Fed. Rep. of Germany

[21] Appl. No.: 78,496

[22] Filed: Sep. 24, 1979

[30] Foreign Application Priority Data

Sep. 27, 1978 [CH] Switzerland ............... 10059/78

[51] Int. Cl.³ .................................................. A61G 1/14
[52] U.S. Cl. ..................................... 433/77; 206/369; 206/558; 206/564
[58] Field of Search ................. 433/77, 79; 206/369, 206/558, 564, 63.5, 562, 563, 368, 379, 363, 370; 422/104; 211/74

[56] References Cited

U.S. PATENT DOCUMENTS

| | | | |
|---|---|---|---|
| 3,102,637 | 9/1963 | Scholl, Sr. | 206/369 |
| 3,295,208 | 1/1967 | Redtenbacher | 433/77 |
| 3,358,826 | 12/1967 | Siegel | 206/368 |
| 3,360,122 | 12/1967 | Rückert | 206/63.5 |
| 3,634,937 | 1/1972 | Green | 433/77 |
| 4,050,894 | 9/1977 | Genis | 206/368 |
| 4,191,291 | 3/1980 | Brown | 206/379 |

FOREIGN PATENT DOCUMENTS 1038714 9/1958 Fed. Rep. of Germany ............ 433/77

OTHER PUBLICATIONS

"Work Simplification in the Dental Office", L & R Manufacturing Co., New Jersey, 10-1968, 93RI-767-1-5-N.
"American Modular Dental Cabinets", Hamilton brochure, 1966, pp. 20-21.

Primary Examiner—Robert Peshock
Assistant Examiner—John J. Wilson
Attorney, Agent, or Firm—Robert E. Burns; Emmanuel J. Lobato; Bruce L. Adams

[57] ABSTRACT

A container for dental equipment is equipped with six minitrays (2 to 7), which can be removed and sterilized individually, each of which comprises a handle (8) on its upper side and legs (9) on its underside. A minitray (2) is provided with elongated recesses (a to f), three similarly constructed minitrays (3 to 5) are provided with holes (9) for receiving root canal instruments and two further minitrays (6, 7) are provided with larger holes (h, k) for receiving glass tubes for holding treatment material. The four minitrays (2 to 5) have substantially the same dimensions, whereas the two latter minitrays (6, 7) are half as wide as the other minitrays.

6 Claims, 9 Drawing Figures

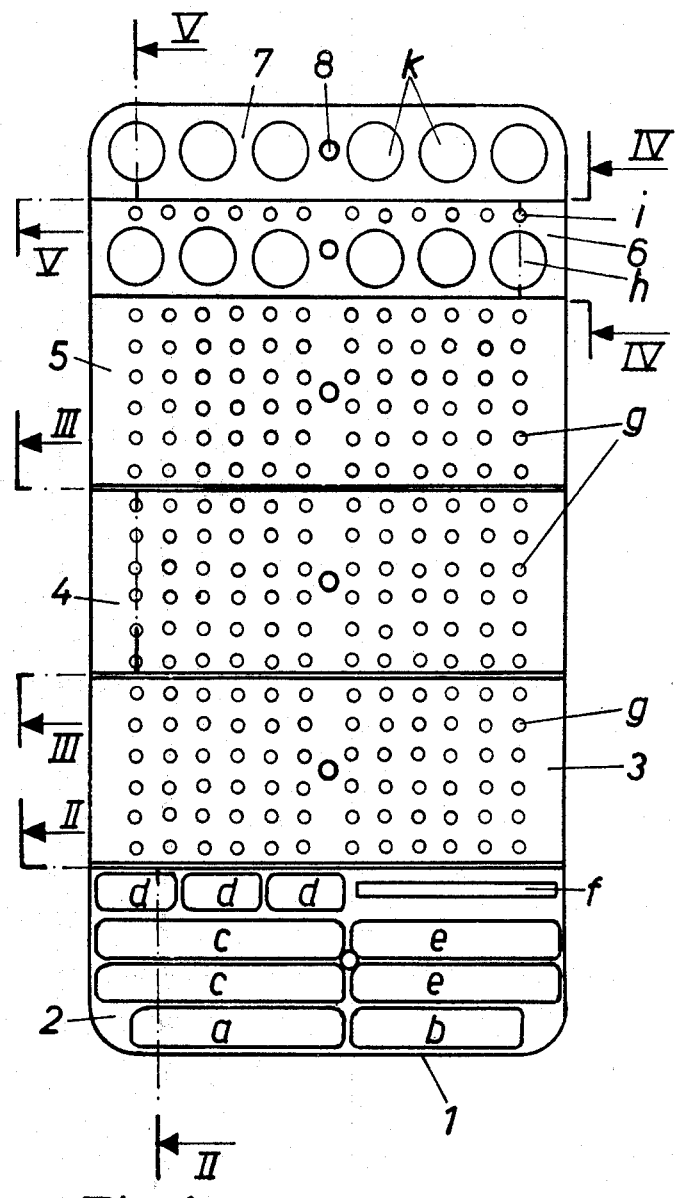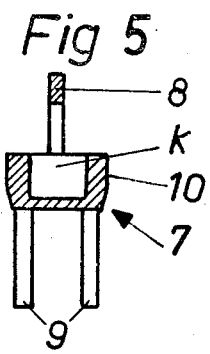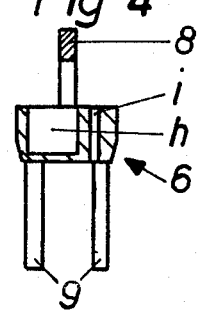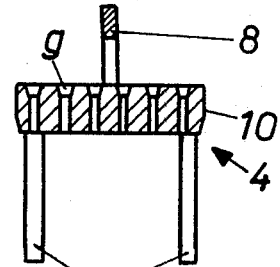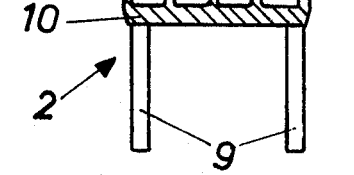

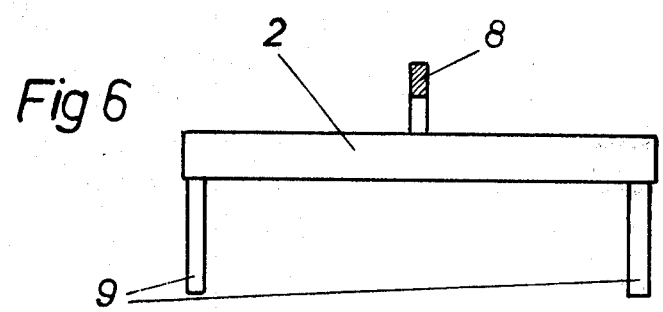
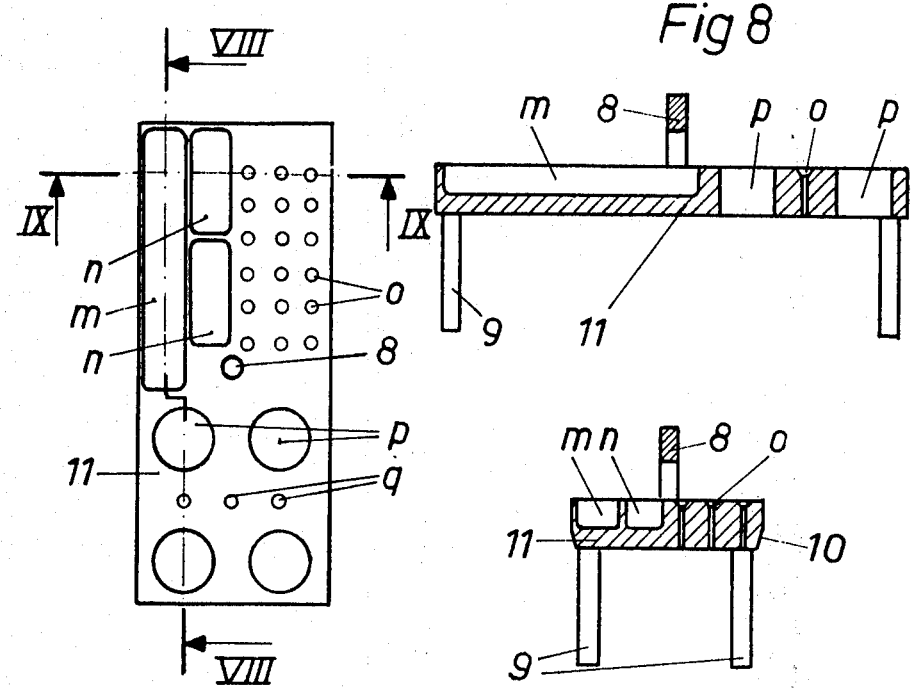

CONTAINER FOR DENTAL EQUIPMENT FOR ROOT-TREATMENT

This invention relates to a container for dental equipment for root-treatment, i.e. to a so-called "endodontic box".

Such containers for holding, inter alia, burr-drills, probes, nerve needles and reamers are known in various forms, and some are provided with inserts, but none has till now been designed to satisfy all of a dentist's requirements as regards the full range of instruments required and allowing for convenient, easy and reliable handling. In particular, due to the construction of existing containers and the arrangement of the instruments therein, it is generally not possible, or only by paying a great deal of attention, due to trouble and difficulty of sorting out of the instruments, to prevent fine instruments from being sterilized several times, and indeed with most containers, it is always necessary to sterilize the entire contents. Due to heating at the time of sterilization, fine instruments become age-hardened and thus when this heating is repeated many times, this leads to a danger of a fracture of the material of the instrument. If, for example, a root-instrument were to break in the root-canal, during a treatment, then this is extraordinarily distressing for the patient and the dentist, because this tooth then frequently has to be extracted.

It is an object of the invention to provide a container which presents to a dentist a complete treatment unit with all the instruments and materials necessary for normal root-treatment disposed in a clearly visible manner, stored and positioned individually by the dentist during each treatment, and which is additionally divided so that, on the one hand, all the sections, in particular the parts used most frequently, can be sterilized individually and, on the other hand, all the parts which cannot be sterilized repeatedly can be removed conveniently and quickly from the container.

According to the present invention there is provided a container for dental equipment for use in root-treatment and having a plurality of inserts located side-by-side and serving to receive the dental equipment, the inserts being constructed as minitrays which can be removed individually and sterilized with each being provided on its upper side with a handle and on its underside with legs, and there being at least three different forms of minitray, whereof the first comprises elongated recesses, for locating instruments, the second comprises holes with diameters of the order of 1 to 2 mm for receiving instruments, and the third comprises holes with diameters of the order of 5 to 20 mm for receiving receptacles for holding treatment material and there being at least one of each form of minitray.

The technical advantages of such a container is that each minitray can be equipped individually with instruments and/or treatment materials, according to a specific function assigned to the latter, and may function both as an instrument store as well as a general purpose tray which can be placed on the work table outside the container and moreover, each minitray can be sterilized separately, so that instruments which are not used and their minitrays are treated carefully and are not sterilised. Also, equipment which should not be sterilized twice can be removed conveniently by lifting its minitray out of the container by its handle.

The three forms of minitray serve to receive the equipment required for the three main stages of a root-treatment, namely instruments for locating a root canal, for the extirpation of the tooth nerve and for measuring the length of the root canal; instruments for enlarging and scraping out the root canal; and materials necessary for drying and filling the canal. Whereas only one minitray of the first form is normally required, three minitrays of the second form are preferably provided in the container and two minitrays of the third form are conveniently provided, since part of the treatment materials belonging to these minitrays, namely in particular gutta-percha sticks, cannot be sterilized twice. Preferably, all minitrays of the first and second forms have the same dimensions, for example, a length of approximately 10 cm and a width of 4 cm, whereas the two minitrays of the third form are half as wide as the other minitrays, so that the minitrays can be exchanged and located individually, and, if necessary, reserve trays of corresponding dimensions can be kept ready for replacing a minitray which is no longer complete or is equipped for special treatment.

A container for receiving the six minitrays conveniently has dimensions of 20 centimeters by 10 centimeters, which corresponds to a standard drawer as used in a dentist's surgery and has a height of approximately 52 mm including the lid.

An embodiment of the invention will now be described, by way of example with reference to the drawings, in which:

FIG. 1 is a plan view of an open container with the minitrays inserted therein,

FIGS. 2, 3, 4 and 5 are sections through the minitrays on lines II—II, III—III, IV—IV and V—V in FIG. 1, FIG. 6 is a side view of the longitudinal side of a minitray, FIG. 7 is a plan view of a reserve tray for a special treatment case and FIGS. 8 and 9 are sections on lines VIII—VIII and IX—IX of FIG. 7.

The container 1 is a rectangular housing of stainless steel, provided with rounded corners, with external dimensions which correspond to standard drawer size, i.e. it is 20 cm long and 10 cm wide and including the lid (not shown) has a height of 5.2 cm. The inside of the housing is filled by six minitrays 2 to 7 of anodized aluminum, which can be removed individually, whereof the minitrays 2 to 5 all have the same dimensions, with a width of 39 mm, while the minitrays 6 and 7 are half as wide as the other minitrays. The minitrays 2 and 7 located on the two narrow sides of the container have a contour adapted to the rounded corners of the container.

As shown in FIGS. 2 to 6, each minitray comprises a handle 8 centrally of its upper side by which it can be removed easily and conveniently from the container, and, on its underside, at the four corners, each minitray comprises four legs 9, by which it can be supported conveniently outside the container on, for example, a worktable. To facilitate their insertion into the container 1, the edges of all the minitrays are provided with a bevel 10 on their longitudinal sides, by which they bear against each other in the container. The height of the minitray plate amounts to 10 mm for example, that of the legs 9 to approximately 24 mm and that of the handle 8 to approximately 15 mm, so that the total height of a minitray amounts to approximately 4.9 cm.

The first form of minitray 2, and of which only one is normally required, serves to receive the instruments for locating a root canal, for the extirpation of the tooth nerve and for measuring the length of the root canal and therefore has elongated recesses a to f for receiving the instruments. Thus, for example, the recesses a and b may receive rose head burrs, the recesses c bevelled probes and measuring probes, the recesses d rubber stoppers, the recesses e nerve needles and the recess f a measuring gauge.

The second form of minitrays 3, 4 and 5, and of which three are preferably provided, receive the instruments for enlarging and scraping out the root canal and for this purpose are provided with holes g having a diameter of 1.5 mm, the upper edge of which is countersunk. All three minitrays 3, 4 and 5, each of which has twelve rows of holes each comprising six holes, in the present example, are constructed in a completely identical manner with the exception of the engraved numbers on one edge of each minitray, which numbers specify the instruments in the holes. The minitray 3 receives nerve needles and machine instruments for example, in the form of reamers, the minitray 4 receives Hedström files and machine instruments in the form of files, and the minitray 5 receives root canal burrs.

The third form of minitrays 6 and 7 serve to receive utensils for drying the nerve canal and for filling the canal. In this example, the minitray 6 is provided with six holes h each having a diameter of 12 mm, which are intended to receive glass flasks or glass tubes for receiving standardized paper points and with twelve holes having a diameter of 1.5 mm for receiving root fillers. The minitray 7 likewise comprises six holes k with diameters of 12 mm, which serve to receive glass tubes or glass flasks for holding standardized gutta-percha sticks, which cannot be sterilized twice and therefore are placed on a separate individual minitray.

If necessary, a reserve tray 11 for special treatment cases (FIGS. 7 to 9) can be provided. Such a reserve tray 11 has the same dimensions as one of the minitrays 3, 4 and 5 and is also provided with a handle 8 on its upper side and with four legs 9 on its underside, and, in this example, has three elongated recesses m or n, an area of three times six holes o having a diameter of 1.8 mm and also for larger holes p having a diameter of 12 mm and finally three holes g each having a diameter of 1.5 mm. In practice, such a reserve tray can be held in readiness advantageously in its own housing.

Reserve trays may also be provided, which correspond to the minitrays 2 to 7, as regards their construction and equipment, for the purpose of replacing a minitray which is no longer complete, so that the container 1 can always be replenished.

The invention is not restricted to the afore-described construction of the minitray and its equipment, since a dentist can equip and dispose each minitray according to his wishes since the individual minitrays are interchangeable. Excluding all parts which cannot be sterilized several times, all instruments and materials to be sterilized before a treatment may be combined on one or more minitrays, which are then subjected to a sterilization process. On the other hand, those parts which are not intended to be sterilized several times, may be placed on a separate minitray and this minitray simply removed from the container, before the entire container with the other minitrays is sterilized. This possibility of convenient individual sterilization means that instruments are treated carefully and therefore, which is extraordinarily important, any danger of a fracture of a fine root canal instrument is substantially reduced.

What is claimed is:

1. A container for dental equipment for use in root-treatment and having a plurality of inserts located side-by-side and serving to receive the dental equipment, the inserts being constructed as minitrays which can be removed individually and sterilized with each being provided on its upper side with a handle and on its underside with legs, and there being at least three different forms of minitray, whereof the first comprises elongated recesses for locating instruments, the second comprises holes with diameters of the order of 1 to 2 mm for receiving instruments, and the third comprises holes with diameters of the order of 5 to 20 mm for receiving receptacles for holding treatment material and there being at least one of each form of minitray.

2. A container according to claim 1, having a substantially rectangular shape contains one first form minitray, three second form minitrays and two third form minitrays, one of the latter also having small holes for receiving root fillers, and all the minitrays being of the same length adapted to the width of the container, the same height and with the exception of the two third form minitrays the same width, the sum of the widths of the latter being equal to the width of the other minitrays, and each third form minitray being half as wide as the other minitrays.

3. A container according to claim 1 or 2, in which the first form minitray is located at one side of the container, the three second form minitrays are located in the central area of the container, and the two third form minitrays are arranged side-by-side at the other side of the container, the outer edges of the minitrays located at the side conforming to rounded corners of the side walls of the container.

4. A container according to claim 1 or 2, in which it is also provided with a further minitray, which has the same dimensions as a second form minitray and can be exchanged for one of these, such further minitray having both elongated recesses and small holes for receiving instruments and larger holes for receiving capillary tubes or other receptacles.

5. A container according to claim 1, in which the edges of the minitrays are bevelled at least on their sides which bear against each other in the container.

6. A container according to claim 1, in which the small holes are countersunk at their upper edges.

* * * * *